United States Patent [19]
Winterer et al.

[11] Patent Number: 5,514,102
[45] Date of Patent: May 7, 1996

[54] PRESSURE MONITORING ENTERAL FEEDING SYSTEM AND METHOD

[75] Inventors: Sean Winterer, Sandy; Chris Dumas, Midvale, both of Utah

[73] Assignee: Zevex Incorporated, Salt Lake City, Utah

[21] Appl. No.: 435,714

[22] Filed: May 5, 1995

[51] Int. Cl.⁶ ................................................. A61M 31/00
[52] U.S. Cl. ............................... 604/67; 604/65; 604/118
[58] Field of Search .................................. 604/65, 30, 31, 604/34, 66, 67, 118, 119, 246

[56]          References Cited

U.S. PATENT DOCUMENTS

| | | |
|---|---|---|
| D. 284,221 | 6/1986 | Kerkut . |
| 4,460,355 | 7/1984 | Layman . |
| 4,515,588 | 5/1985 | Amendolia . |
| 4,559,034 | 12/1985 | Kirita et al. . |
| 4,613,325 | 9/1986 | Abrams . |
| 4,784,576 | 11/1988 | Bloom et al. . |
| 4,784,577 | 11/1988 | Ritson et al. . |
| 4,838,865 | 6/1989 | Flank et al. ................ 604/65 |
| 4,863,425 | 9/1989 | Slate et al. ................ 604/65 |
| 4,950,244 | 8/1990 | Fellingham et al. . |
| 4,976,687 | 12/1990 | Martin . |
| 4,994,035 | 12/1991 | Mokros . |
| 5,037,386 | 8/1991 | Marcus et al. . |
| 5,096,385 | 3/1992 | Georgi et al. . |
| 5,098,384 | 3/1992 | Abrams . |
| 5,098,387 | 3/1992 | Wiest et al. ................ 604/31 |
| 5,137,522 | 8/1992 | Bron . |
| 5,195,960 | 3/1993 | Hossain et al. ............. 604/34 |
| 5,312,334 | 5/1994 | Hara et al. . |
| 5,336,181 | 8/1994 | Nakao et al. . |
| 5,346,477 | 9/1994 | Edwards et al. . |

*Primary Examiner*—Corrine M. Maglione
*Assistant Examiner*—N. Kent Gring
*Attorney, Agent, or Firm*—Thorpe North & Western

[57]          ABSTRACT

A pressure monitoring enteral feeding system and method are disclosed including a housing having a pair of channels for receiving a pump tubing segment which connects an intake line and an output line of a delivery set, and for holding the pump tubing segment adjacent a motor unit. A pair of pressure sensors are disposed along the channels to monitor the pressure in the pump tubing segment so as to warn a user when an undesirable pressure has developed either upstream or downstream from the motor unit, and to adjust rate based on the upstream pressure. The housing may also include a lockable cover to securely hold the pump tubing segment in the channels and in firm contact with the pressure sensors.

21 Claims, 6 Drawing Sheets

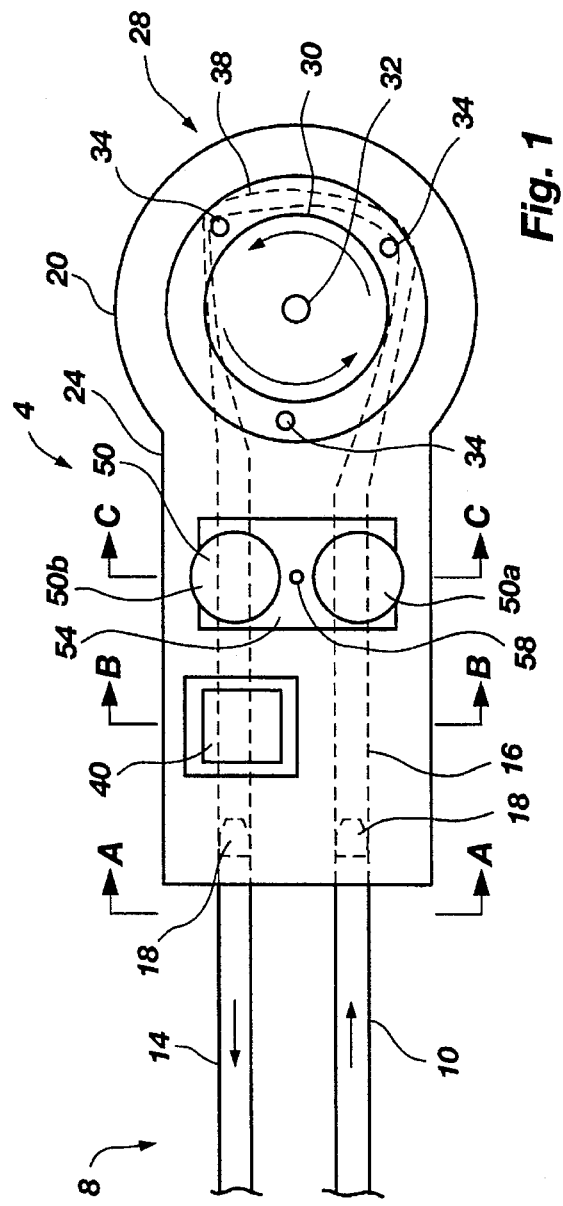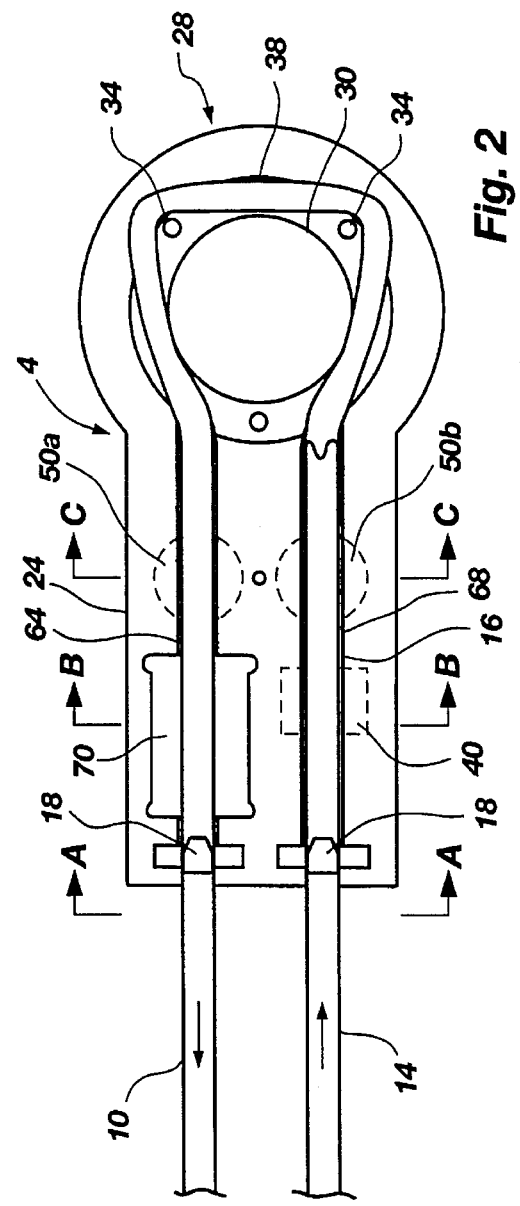

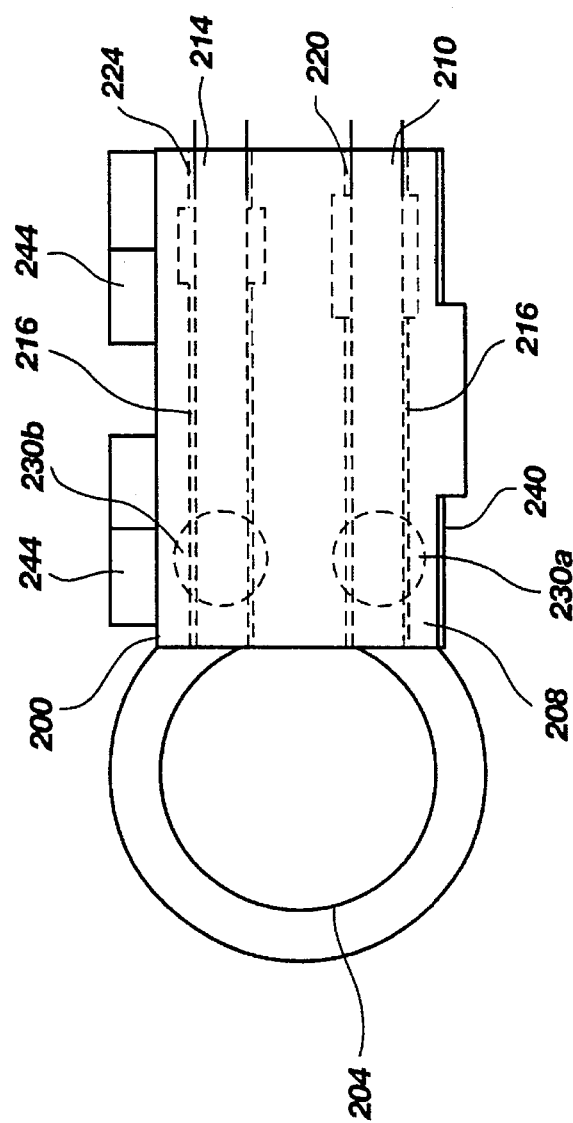
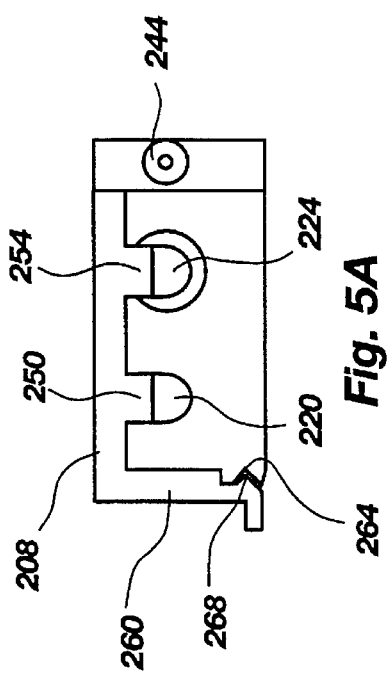
Fig. 5
Fig. 5A

PRESSURE MONITORING ENTERAL FEEDING SYSTEM AND METHOD

BACKGROUND OF THE INVENTION

The present invention relates to systems for feeding solutions to patients, and in particular to an enteral feeding system using pressure sensors to ensure that delivery of the solution by an enteral feeding pump is within desired parameters.

An enteral feeding system is used to provide nutrient solutions to patients who, for one reason or another, are unable to eat for themselves. Such a system typically includes a pump which is attached to an input tube connected to a supply container and to an output tube which is connected to a patient. The pump draws nutrient solution from the supply container and delivers the solution to the patient. By adjusting the speed at which a motor in the pump rotates a rotor, medical personnel can adjust the pump to deliver a predetermined amount of nutrient solution (or even medication) at a desired rate. The use of various types of enteral feeding systems is well known in the medical arts.

A significant problem with currently available enteral feeding systems, is that the intake and output tubes may become occluded. Occlusion can occur, for example, if a fibrous substance is included in the solution and somehow combines to interfere with flow through the tube. Occlusion can also occur if a tube is bent sufficiently to interfere with flow therethrough, or if a roller clamp (as is commonly used for intravenous applications) is not sufficiently loosened.

If the intake tube becomes occluded, insufficient solution may be supplied to the pump, and thus to the patient. If the output tube becomes occluded, the flow of solution may be blocked, or the solution may be delivered at unusually high pressures. Additionally, medical personnel may fail to notice that the supply container is out of solution, or may not properly mount the intake and/or output tubes in the pump, thereby preventing the proper amount of solution from being delivered to the patient. Any of these scenarios can have tragic consequences if medical personnel are not alerted in time.

To overcome these concerns, there is a need for a system and method for determining discrepancies due to occlusions and/or improper fitting of pumps and intake/output tubes so that patients will not be endangered.

OBJECTS AND SUMMARY OF THE INVENTION

It is an object of the present invention to provide an enteral feeding system including an enteral feeding pump having at least one sensor to ensure that the intake and output tubes are properly attached to the feeding pump.

It is another object of the present invention to provide an enteral feeding system including an enteral feeding pump having upstream and downstream sensors for determining the extent of occlusion of the inlet and/or output tubes connected to the pump.

It is another object of the present invention to provide an enteral feeding system having sensors on the intake and output tubes so as to determine location of an occlusion in the event occlusion occurs.

It is another object of the present invention to provide an enteral feeding pump incorporating such sensors which may be used with conventional disposable delivery sets.

The above and other objects features and advantages of the present invention will become apparent in an enteral feeding system including a pump which has a motor in communication with an intake tube for receiving a nutrient solution from a supply container and an output tube for delivering solution to the patient. The enteral feeding system also includes a pair of pressure sensors placed along the delivery set for monitoring the tubes and determining if there is an occlusion in the system.

In accordance with one aspect of the invention, a proximal pressure sensor is placed along the intake tube and a distal pressure sensor is placed along the output tube so as to monitor the pressure in each tube and thereby determine if either tube has an occlusion, and to determine if either tube is not properly attached to the enteral feeding pump.

In accordance with another aspect of the invention, the alternating current output of the pressure sensors caused by changing tension on the tubing is monitored so as to indicate proper operation of the pressure sensors.

In accordance with yet another aspect of the invention, the system includes an adaptation mechanism to adjust the pump rotation to correspond to changed proximal pressure readings, such as those caused by a change in supply container height or fluid viscosity.

BRIEF DESCRIPTION OF THE DRAWINGS

The above and other objects, features and advantages of the invention will become apparent from a consideration of the following detailed description presented in connection with the accompanying drawings in which:

FIG. 1 shows a bottom fragmented view of an enteral feeding system including an enteral feeding pump connected to intake and output tubes;

FIG. 2 shows a top fragmented view of an enteral feeding system including an enteral feeding pump connected to intake and output tubes;

FIGS. 5 and 5A show a preferred embodiment of an enteral feeding pump made in accordance with the principles of the present invention, the pump including a cover to hold the inlet and output tubes in a desired position;

DETAILED DESCRIPTION

Figure 3A:
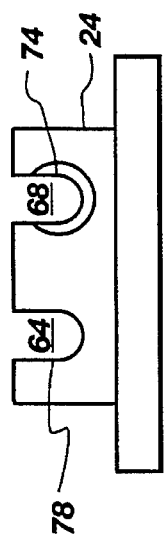
FIG. 3A shows an end view of the enteral feeding pump of the present invention taken along the line A.

Reference will now be made to the drawings in which the various elements of the present invention will be given numeral designations and in which the invention will be discussed so as to enable one skilled in the art to make and use the invention. Referring to FIG. 1, there is shown a fragmented top view of an enteral feeding system, generally indicated at 4, having a delivery set 8 including an intake (upstream) tube 10 and an output (downstream) tube 14 connected together by a pair of connector 18 and a pump tubing segment within an enteral feeding pump 20. The position of the pump tubing segment disposed inside of the pump 20 is represented by the dashed lines 16. Typically an opposing end (not shown) of the inlet tube 10 would be connected to a supply container (also not shown) and an opposing end (not shown) of the output tube 14 would be attached to a patient so as to deliver solution provided by the pump 20.

The enteral feeding pump 20 includes a housing 24 with a conventional motor unit, generally indicated at 28. The motor unit 28 includes a rotor 30 with a plurality of peristaltic rollers 34 disposed about an exterior of the rotor to move liquid through the enteral feeding pump 20. The rotor 30 is connected by a shaft 32 to a motor (not shown). The section 38 of the pump tubing segment 16 is disposed about the rotor 30 and rollers 34 and is usually made of a flexible silicon material. Rotating the rotor 30 in the direction indicated by the arrows directionally squeezes the tube section 38 and causes solution to be pushed out of the enteral feeding pump and through the output tube 14. Typically, each rotation of the rotor will move about ¼ ml of solution.

Also shown in FIG. 1 is an air detector 40 provided in a distal position (down stream) to the motor unit 28 along the output tube 14 to warn medical personnel of an empty supply container. The above described elements of an enteral feeding pump are generally known to those skilled in the art.

In addition to these elements, the enteral feeding pump 20 of the present invention includes a pair of pressure sensors 50. In a preferred embodiment, two pressure sensors 50a and 50b are disposed along the pump tubing segment 16 adjacent the intake/output tubes, 10 and 14 in order to 1) ensure that the tubes are properly mounted in the pump 20; and 2) detect any occlusions in the intake tube 10 or the output tube 14 of the delivery set 8. A retention plate 54 (FIG. 1) is attached to the housing 24 by a screw 58 to hold the pressure sensors 50a and 50b in place. As will be appreciated, if the sensors are not securely held, any readings obtained will be unreliable.

As the pump 20 operates, the motor unit 28 mechanically blocks the tube section 38 and pushes fluid within the tube toward the output tube 14. During this process, the pump tubing segment 16 stretches and contracts. The stretching and contracting can be measured by the pressure sensors. This is an expected signal and its absence is interpreted by a control processor (discussed below) as a failure of the corresponding sensor.

While discussed herein as a pump tubing segment, the tubing passing through the pump 20 could be an intake line and an output line connected together. In such a situation, each would preferably be made of the same materials as the pump tubing segment 16.

In FIG. 2, there is shown a fragmented top view of the enteral feeding system 4. As is apparent, the pump tubing segment 16 is attached to the intake tube 10 and the output tube 14, and extends along the housing 24 to a position about the motor unit 28. The housing 24 has channels 64 and 68, respectively, for receiving the pump tubing segment 16 so that it is disposed adjacent to the respective pressure sensors, 50a and 50b.

In FIG. 2 there is also shown a void 70 formed in the channel 64 designed to receive a pinch clip occluder (not shown) which may be used with the pump tubing segment 16 to prevent solution from flowing through the pump tubing segment until the clamp has been released. (An example of such a clamp is contained in U.S. Ser. No. 08/410,912 filed on Mar. 27, 1995, pending). Thus, unless the pump tubing segment 16 has been properly fitted into the channel 64 so that the clamp fits within void 70 and the pump door closed properly, solution will not flow through the pump 20. This is important because medical personnel occasionally fail to properly thread the pump tubing segment 16 through the enteral feeding pump 20 or to close a roller clamp, etc., prior to opening the pump door.

Failure to properly connect the system 4 can result in a situation known as free flow wherein the rate at which solution is supplied to the patient is not dependant on the motor unit 28, but rather on the force of gravity and on the amount of solution in the supply container. If the supply container is disposed above the patient, a much greater quantity of solution will usually enter the patient than would have had the pump tubing segment 16 been properly mounted in the channels 64 and 68 of the pump 20 so that flow through the section 38 was controlled by the motor 28. The large infusion of solution can cause serious complications for the patient, and occasionally can result in death. By using a clamp which is released by fitting it within the void 70 or some similar arrangement, this free flow condition can be avoided.

The pressure sensors 50a and 50b compliment this feature. The risk of using a clamp which is biased in a closed position is that fluid flow through the device will be halted if the clamp has not been moved into an open position. This can prevent fluid flow even if the remainder of the delivery set is properly mounted, and can harm the patient if undiscovered. In such a situation, the pressure sensors 50a and 50b will indicate an occlusion, warning medical personnel that the pump 20 should be checked.

Referring now to FIG. 3A, there is shown an end view of the pump housing 24 taken along line A of FIGS. 1 and 2. The housing 24 has a pair of openings 74 and 78 which lead into channel 68 and 64, respectively, which are positioned generally parallel to one another. When the intake tube 10 and the output tube 14 (FIGS. 1 and 2) are nested into the channels 64 and 68, they are held by the sides of the openings 74 and 78.

Figure 3B:
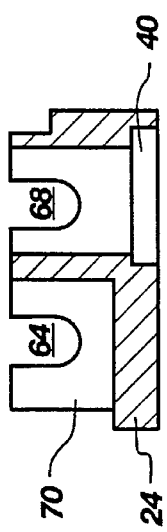
FIG. 3B shows a cross-sectional view of the enteral feeding pump of the present invention taken along the line B.

In FIG. 3B, there is shown a cross-sectional view of the housing 24 taken along the line B of FIGS. 1 and 2. The air detector 40 is disposed about channel 68, and the void 70 is formed about channel 64 as was discussed with respect to FIG. 2.

Figure 3C:
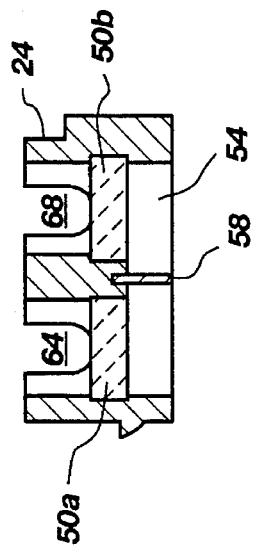
FIG. 3C shows a cross-sectional view of the enteral feeding pump of the present invention taken along the line C.

Referring to FIG. 3C, the pressure sensors 50a and 50b extend up into the channels, 64 and 68 respectively, so that sensor 50b will contact the pump tubing segment 16 near the output line 14 (FIGS. 1 and 2) and sensor 50a will contact the pump tubing segment near intake line 10 (FIGS. 1 and 2). The sensors 50a and 50b press up on the tubes sufficiently so that they can determine the pressure which exists in the tube. As will be discussed with respect to FIGS. 5 and 6, the tubes can also be held down firmly against the sensors.

A decrease in the pressure on sensor 50a indicates that pressure has fallen in the intake tube 10. This indicates that either the intake tube 10 is occluded on an upstream side of the sensor, or that the fluid viscosity or head height has decreased. An increase in the pressure on sensor 50b indicates that there is an occlusion in output line 14. Thus, by observing the output of each sensor 50a and 50b, medical personnel can be assured that solution is being delivered to the patient at the proper pressure. Those skilled in the art will recognize that each rotation of the motor unit will cause temporary increases in pressure on sensor 50b and decreases on sensor 50a. Part of the change in pressure occurs because of changes on the tension of the tubing. Rather than filtering out this component, it is monitored to ensure that the pressure sensors 50a and 50b are functioning properly. Additionally, rather than ignoring the sharp peak caused by each movement of the rotor 30, the entire curve is monitored and an average taken. If the average exceeds a predefined threshold, an alarm is activated. Such a method, however, prevents a momentary occlusion alarm as may be caused by a patient's movement.

As was discussed regarding FIG. 1, the sensors 50a and 50b are held in place by the retention plate 54 which is held to the housing 24 by screw 58. A silicone boot (not shown) may be included for sealing and protecting the sensors 50a and 50b. In the event a pressure sensor 50a or 50b malfunctions, the plate 58 (and boot) can be removed by unscrewing screw 58, thereby enabling the sensor to be replaced.

Figure 4A:
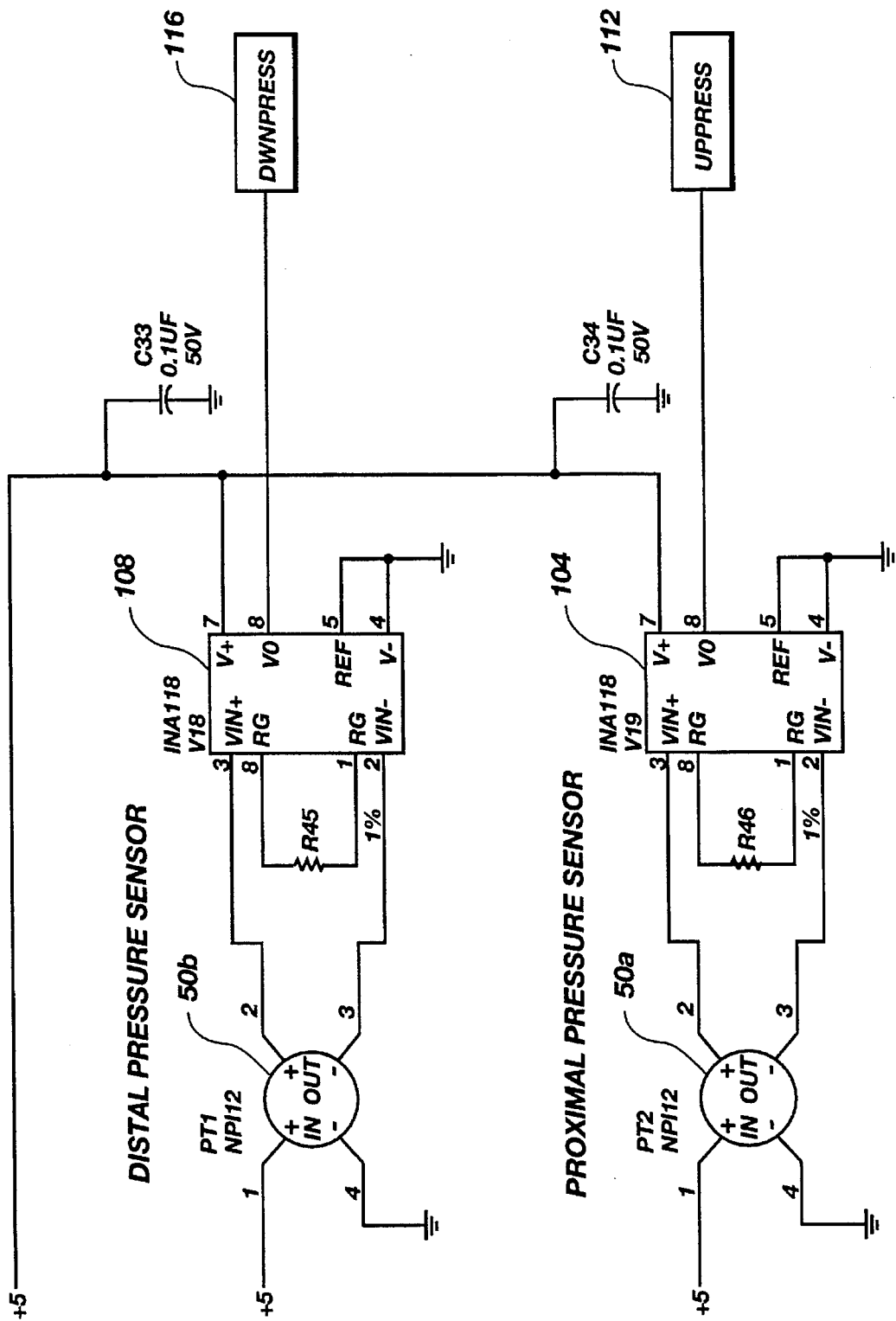
FIGS. 4A and 4B are schematics of the circuitry used to monitor the pressure of solution passing through the intake and output tubes.
Figure 4B:
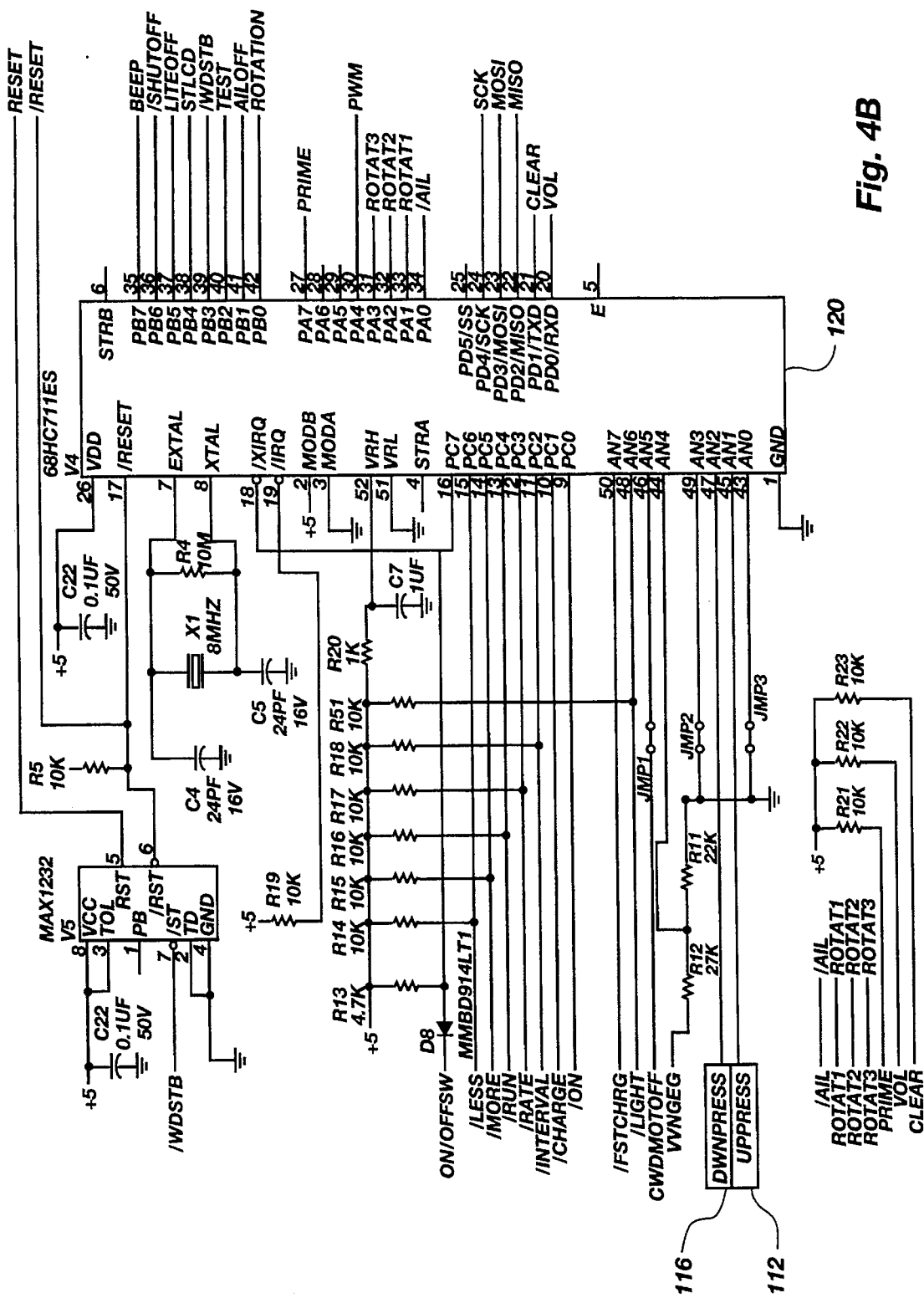

Referring now to FIG. 4A, there is shown a schematic view of the circuitry for the pressure sensors 50a and 50b. Each sensor 50a and 50b is connected to a respective preprocessor, 104 and 108. The preprocessors 104 and 108 are, in turn, connected to input/output lines 112 and 116 which communicate with a control processor 120 which is shown in FIG. 4B. By monitoring the readings from the pressure sensors 50a and 50b and preprocessors, the control processor 120 can determine whether an occlusion exists, either upstream or downstream, or whether the delivery set 8 has been loaded properly. It should be appreciated by those skilled in the art that combined circuitry could be used to monitor the pressure sensors and other dynamics of the system, such as the position of the rotor 30 (FIGS. 1 and 2) and the speed at which it rotates. By incorporating all of this information, a single set monitor could be used to supply all information needed about the enteral feeding system 4 and to allow the user to modify the dynamics of the system as needs change.

Additionally, the control processor could be preprogrammed to control the rotor in response to information obtained from the sensors 50a and 50b. Thus, for example, if an occlusion were detected downstream from the motor unit 28, the control processor 120 may stop operation of the rotor and emit a warning to medical personnel that the pump has shut down due to an occlusion. Likewise, changes in upstream pressure sensed by the sensors 50a and 50b may be used by the control processor to control the rotation rate or the motor unit to ensure consistent delivery of the fluid.

Referring now to FIGS. 5 and 5A, there is shown a top view and an end view of an enteral feeding pump 200. The pump includes a motor unit 204 and all of the other features discussed in FIGS. 1 and 2. The primary difference between the pump 200 in FIG. 5 and the pump 20 in FIGS. 1 and 2, is that pump 200 has a cover 208 for ensuring that the pump tubing segment 216 is properly positioned in the channels 220 and 224, and that the pump tubing segment is in firm contact with the sensors 230a and 230b.

The cover 208 is attached to a base portion 240 of the pump 200 by one or more hinges 244 so as to enable the cover to be rotated between an open position, in which the channels 220 and 224 are accessible, and a closed position in which they are not. The cover 208 has a pair of projections 250 and 254 which extend downwardly into the channels 220 and 224 so as to hold the pump tubing segment 216 firmly against the sensors 230a and 230b. Having the tubes 210 and 214 in place so that the pump tubing segment 216 is in firm contact with the pressure sensors 230a and 230b allows for more accurate readings.

The cover 208 also has a clip portion 260 which extends along the base portion 240 to a small groove 264 formed therein. The clip portion 260 of the cover 208 is typically resilient, and a flange 268 extending from the clip portion will nest in the groove 264 so as to hold the cover in place. To release the cover 208 and provide access to the channels 220 and 224 in the base portion 240, the clip portion 260 need only be bent so that the flange 268 does not nest in the groove 264. The cover 208 may then be pivoted out of the way. When the tubes 210 and 214 have been adjusted, or replaced, etc., the cover 208 need merely be rotated into the position shown in FIG. 5, and a small amount of force applied until the flange 268 nests in the groove 264 to hold the cover shut. Once the tubes 210 and 214 are placed in the channels 220 and 224, and the cover 208 is shut, the tubes are locked in place, and may only be removed by opening the cover.

Figure 6:
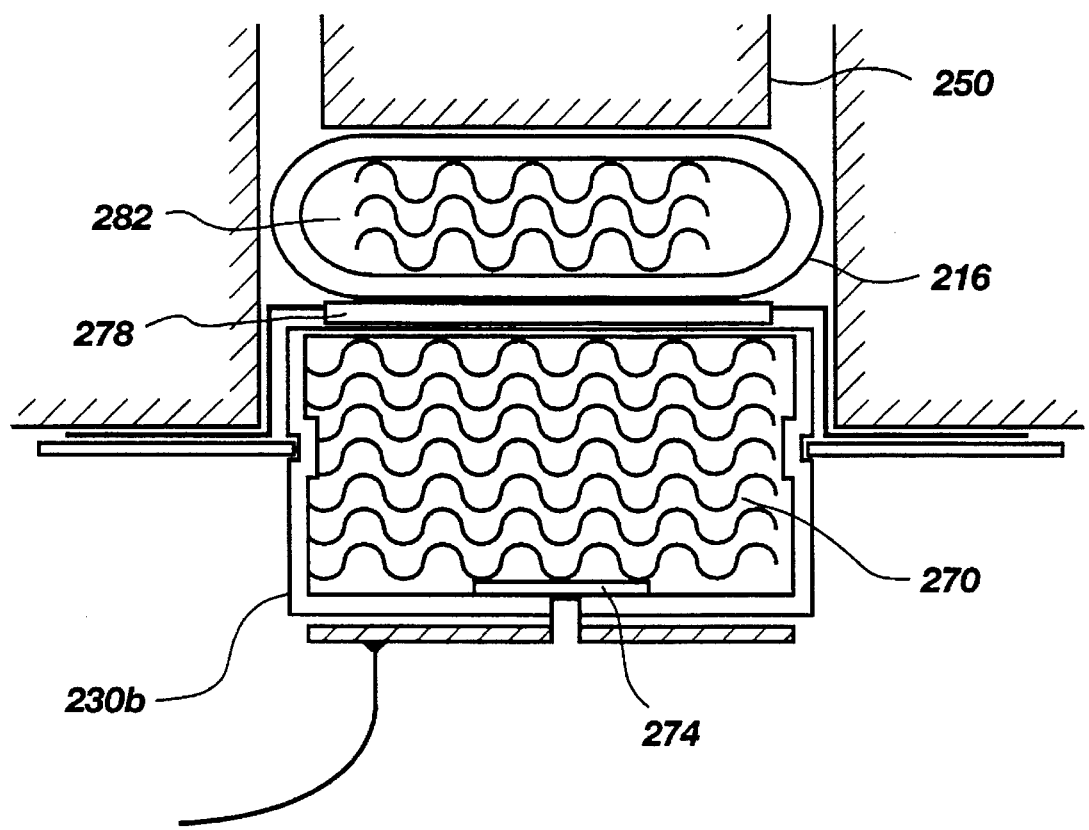
FIG. 6 shows a fragmented, cross-sectional view of the pressure sensor with a tube mounted adjacent thereto.

Referring now to FIG. 6, there is shown a close-up, fragmented cross-sectional view of a pressure sensor 230b and the surrounding area. The pressure sensor includes an oil filled reservoir 270 and a pressure sensor chip 274. A silicone gasket 278 fits between the pressure sensor 230b and the tube 216. The tube 216 is held in place by the projection 250. The partially collapsed tube 216 will exert pressure on the sensor 230b. When there is fluid 282 in the tube 216, increases in fluid pressure will be detectable by the pressure sensor 230b which communicates the increase to the control processor 120 (FIG. 4B). If the delivery set 8 (FIG. 1) were not loaded properly, the pressure sensor 230b would send a signal showing no pressure on the sensor chip 274. The control processor 120 would then send a user identifiable signal indicating that the delivery set is not properly loaded. If an occlusion occurs downstream, the sensor 230b will send a signal to the control processor 120 (FIG. 4B) indicating the existence of an occlusion. While the sensor 230b shown in FIG. 6 is believed to be the preferred embodiment, those skilled in the art will be aware of numerous other types of pressure sensors which may be used to achieve the functions of the present invention.

In the manner set forth above, an Enteral Feeding System and Method is disclosed including an intake tube, an output tube and a pump tubing segment, along which an enteral feeding pump is disposed. A pair of pressure sensors are provided to ensure that the pump is operating properly, and the intake and/or output lines are not occluded. Those skilled in the art will recognize numerous other modifications which could be made while remaining within the scope and spirit of the invention. The appended claims are intended to cover such modifications.

What is claimed is:

1. A medical fluid delivery system comprising:

a motor unit for pumping medical fluids;

a disposable delivery set for engagement with said motor unit for conveying medical fluids disposed with the delivery set as the motor unit periodically engages the delivery set;

housing means disposed adjacent the motor unit for receiving at least a portion of said delivery set; and pressure sensing means disposed along the delivery set for determining pressure of fluids within the delivery set and for determining whether the delivery set is properly loaded within the housing means, the pressure sensing means comprising at least two pressure sensors, a first sensor being disposed so as to contact a portion of the delivery set proximal (upstream) from the motor unit, and a second sensor being disposed so as to contact a portion of the delivery set distal (downstream) from the motor unit.

2. The medical fluid delivery system of claim 1, wherein the pressure sensing means produces signals indicating pressure in the delivery set, and wherein the system further comprises, pump control means operationally connected to the pressure sensing means and the motor unit, for selectively changing operation of the motor unit in response to signals received from the pressure sensing means.

3. The medical fluid delivery system of claim 2, wherein the signals produced by the pressure sensing means include an AC component indicative of changing tension on the delivery set, and wherein the pump control means is responsive to the AC component of said pressure sensing means.

4. The medical fluid delivery system of claim 1, wherein the motor unit comprises a rotor mounted on the housing means and rotated by said motor unit and for receiving a portion of said delivery set so as to form a peristaltic pump.

5. The medical fluid delivery system of claim 4, wherein the sensors emit signals indicative of pressure within the delivery set, and wherein rotation of said motor unit is responsive to said signals.

6. The medical fluid delivery system of claim 4, wherein the first sensor is responsive to occlusions in the delivery set upstream from the rotor, and wherein the second sensor is responsive to occlusions in the delivery set downstream from the rotor.

7. The medical fluid delivery system of claim 6, wherein the pressure sensing means further comprises a user perceptible signal.

8. The medical fluid delivery system of claim 7, wherein both the first and second sensors are responsive to improper loading of the delivery set, such that improper loading of the delivery set causes the pressure sensing means to emit a user perceptible signal.

9. The medical fluid delivery system of claim 1, wherein the housing means comprises a pair of channels disposed in a generally parallel orientation for receiving a portion of the delivery set and holding said portion of the delivery set adjacent the motor unit.

10. The medical fluid delivery system of claim 9, further comprising cover means for holding the portion of the delivery set within the channels.

11. The medical fluid delivery system of claim 9, wherein the pressure sensors of the pressure sensing means are disposed along the channels.

12. An enteral feeding pump for attachment along a delivery set for delivering fluid to a patient having an intake line, an output line and a pump tubing segment connecting the intake and output lines, the feeding pump comprising:

a housing having a first channel for receiving an upstream portion of the pump tubing segment, a second channel for receiving a downstream portion of the pump tubing segment, a selectably engageable cover means for holding the pump tubing segment in the first and second channels and a motor unit disposed adjacent to the first and second channels so as to contact the pump tubing segment functionally between the intake line and output line when said pump tubing is disposed in the first and second channels, pressure sensing means including a first pressure sensor disposed in the housing along the first channel responsive to the nonpresence of the upstream portion of the pump tubing segment within the first channel and responsive to changes in pressure within the upstream portion of the pump tubing segment, and a second pressure sensor disposed in the housing along the second channel responsive to the nonpresence of the downstream portion of the pump tubing segment within the channel and responsive to pressure changes within the downstream portion of the pump tubing segment, and control means in communication with the pressure sensing means for emitting a user identifiable signal when the pump tubing segment is not disposed in the first channel, when the pump tubing segment is not disposed in the second channel, and when pressure in the pump tubing segment changes beyond a predetermined threshold.

13. The enteral feeding pump of claim 12, wherein the cover means comprises at least one projection for holding the upstream portion of the pump tubing segment in contact with the pressure sensing means.

14. The enteral feeding pump of claim 13, wherein the cover means comprises at least one projection for holding the downstream portion of the pump tubing segment in contact with the pressure sensing means.

15. The enteral feeding pump of claim 12, wherein the pressure sensing means conveys signals to the control means indicative of pressures sensed by the pressure sensing means, and wherein the pump further comprises a motor unit including a rotor means, the motor unit being disposed in communication with the control means for selectively controlling rotation of the rotor means responsive to signals received from the pressure sensing means.

16. The enteral feeding pump of claim 15, wherein the motor unit prevents the rotor means from rotating in response to signals from the control means indicative that the pump tubing segment is not properly loaded in the housing.

17. The enteral feeding pump of claim 15, wherein the motor unit prevents the rotor means from rotating in response to signals from the control means indicative that an occlusion exists along the delivery set.

18. The enteral feeding pump of claim 15, wherein the motor unit adjusts a rotation rate of the rotor means in response to signals from the control means indicative that an upstream pressure change has occurred.

19. A medical fluid delivery system comprising:

a motor unit for pumping medical fluids;

a disposable delivery set disposed so as to engage said motor unit such that rotation of the motor unit compresses the delivery set to thereby conveying medical fluids through the delivery set;

housing means disposed adjacent the motor unit for receiving at least a portion of said delivery set; and pressure sensing means disposed in contact with the delivery set for determining tension pressure of fluids within the delivery set and for determining whether the delivery set is properly loaded within the housing means, the pressure sensing means comprising at least two pressure sensors, a first sensor being disposed in contact with the delivery set proximal (upstream) from the motor unit, and a second sensor being disposed in contact with the delivery set distal (downstream) from the motor unit.

20. The medical fluid delivery system of claim 19, wherein the pressure sensing means produces signals indicating pressure within the delivery set, and wherein the system further comprises, pump control means operationally connected to the pressure sensing means and the motor unit, for selectively changing operation of the motor unit in response to signals received from the pressure sensing means.

21. The medical fluid delivery system of claim 19, wherein the signals produced by the pressure sensing means include an AC component indicative of changing tension on the delivery set, and wherein the pump control means is responsive to the AC component of said pressure sensing means.

* * * * *